United States Patent [19]

Krishnan

[11] Patent Number: 5,184,191
[45] Date of Patent: Feb. 2, 1993

[54] SAMPLE TABLE FOR MULTI-MODE SPECTRUM ANALYSIS

[75] Inventor: Krishnaswamy Krishnan, Norwell, Mass.

[73] Assignee: Bio-Rad Laboratories, Inc., Hercules, Calif.

[21] Appl. No.: 672,518

[22] Filed: Mar. 20, 1991

[51] Int. Cl.⁵ .............................. G01N 21/01
[52] U.S. Cl. .................... 356/244; 356/346
[58] Field of Search .................. 356/244, 346

[56] References Cited

U.S. PATENT DOCUMENTS

| | | | |
|---|---|---|---|
| 4,591,266 | 5/1986 | Doyle | 356/346 |
| 4,653,878 | 3/1987 | Nakasato et al. | 350/520 |
| 4,657,390 | 4/1987 | Doyle | 356/244 |
| 4,740,082 | 4/1988 | Young | 356/346 |
| 5,048,970 | 9/1991 | Milosevic et al. | 356/244 |

*Primary Examiner*—Richard A. Rosenberger
*Attorney, Agent, or Firm*—Townsend and Townsend

[57] ABSTRACT

Apparatus for holding and positioning samples of material in a spectrometer includes a sample holding table, a first rotatable platform, and a second rotatable platform. An input optical train mounted on the first platform directs the beam from the spectrometer to the sample. An output optical train mounted to the second platform directs the beam from the sample to a detector. When the first and second platforms are parallel to each other, the input optical train directs the spectrometer beam directly to the output optical train, so that a transmission spectrum may be taken. When the platforms are not parallel to each other, the input optical train directs the spectrometer beam downwardly, and it is only upon reflection from the sample that the beam is directed to the output optical train, so that a reflectance spectrum may be taken.

4 Claims, 3 Drawing Sheets

SAMPLE TABLE FOR MULTI-MODE SPECTRUM ANALYSIS

BACKGROUND OF THE INVENTION

The present invention is in the field of spectrometers and spectrum analysis. In particular, it relates to apparatus for holding and positioning samples for spectrum analysis.

Spectrometers and their use in analyzing the chemical composition of unknown substances are known. In spectrum analysis, a beam of light is passed through a substance, the spectrum of the light transmitted through the substance indicating the composition of the substance. In addition to a transmission spectrum, the spectrum of light reflected off the substance can also be used to determine the substance's composition.

Although hardware exists which enables the user of a spectrometer to obtain either a reflectance or transmission spectrum, no known apparatus permits the simultaneous or near simultaneous acquisition of both types of spectra. As each spectrum offers important information about the composition being tested, obtaining as many possible spectra using as many different modes of spectrum generation as possible in as little time as possible has important benefits to the tester.

SUMMARY OF THE INVENTION

The present invention, in a preferred embodiment, comprises an apparatus for holding and positioning samples of material to allow obtaining both transmission and reflectance spectra in a very limited amount of time.

The apparatus comprises a sample holding table, which mounts within a spectrometer, a first rotatable platform, and a second rotatable platform. The first platform has the input optical train mounted thereon, the input optical train comprised of at least two flat mirrors and one concave mirror. The input optical train directs the beam from the spectrometer onto the sample. The second platform has the output optical train mounted thereon, the output optical train comprised of at least two flat mirrors, one of which is adjustable, and a concave mirror. The output optical train focuses the beam from the sample onto a detector. The first rotatable platform also may have an adjustable beam polarizer mounted thereon for polarizing the incoming beam of the spectrometer.

As the first and second rotatable platforms are independently variable in position, it is possible to reconfigure the present invention from the position needed to obtain a transmission spectrum to the position needed to obtain a reflectance spectrum in a very short amount of time. Additionally, the present invention also has a mounting means for a beam attenuating device for preventing detector saturation or for providing masking capability for isolation and examination of selected portions of the sample.

These features and others of the present invention will now be described in detail, with reference to the figures described below.

DESCRIPTION OF THE SPECIFIC EMBODIMENT

The present invention is an accessory that mounts in the sample compartment of a spectrometer.

Figure 1:
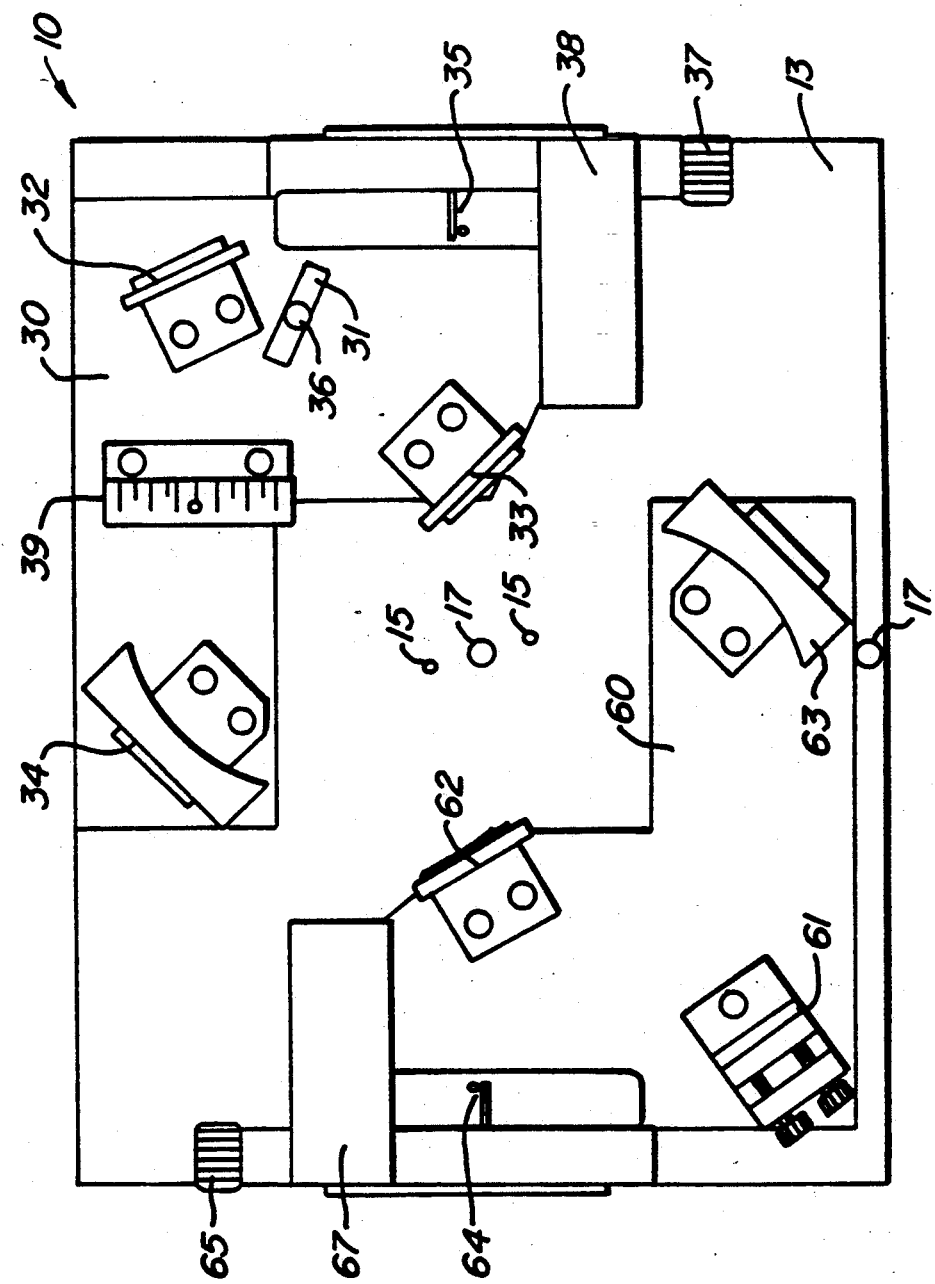
FIG. 1 is an overhead view of the present invention.

As shown in FIG. 1, a preferred embodiment of the present invention 10 comprises a baseplate 13 having sample holder mounting pins 15, compartment mounting pins 17, and first and second rotatable platforms, respectively numbered 30 and 60, mounted thereon.

First rotatable platform 30 comprises a beam input aperture 31, a pair of input flat mirrors 32 and 33, an input toroidal mirror 34, an angle selection lever 35, an aperture holder 36, a thumbscrew 37, a handle 38, and a rotatable polarizer 39. The first rotatable platform is pivotally mounted to baseplate 13 so that the input optical train, which includes aperture 31, mirrors 32, 33 and 34, and, in some cases, polarizer 39, can be pivoted from parallel to the plane defined by baseplate 13 to nearly perpendicular thereto. As the mirrors and polarizer are all fixed to the first rotatable platform, they remain in fixed relation to one another as the first rotatable platform is pivoted.

Second rotatable platform 60 comprises an adjustable flat mirror 61, a flat mirror 62, a toroidal mirror 63, an angle selection lever 64, a thumbscrew 65, a beam output aperture 66, and a handle 67. The second rotatable platform 60 is pivotally mounted on baseplate 13 so that the output optical train mounted on the second rotatable platform, which comprises mirrors 61, 62 and 63 and aperture 66, can be pivoted from a position parallel to the plane defined by baseplate 13 to a position nearly perpendicular to the baseplate. Adjustable mirror 61 is adjusted during initial calibration of the present invention.

Figure 2A:
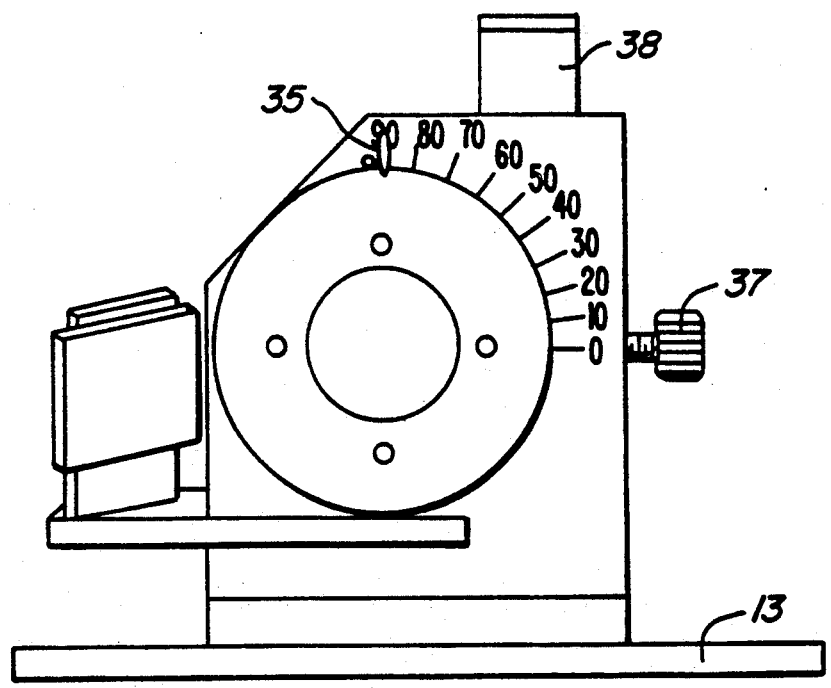
FIGS. 2A and 2B are side views of the first rotatable platform.
Figure 2B:
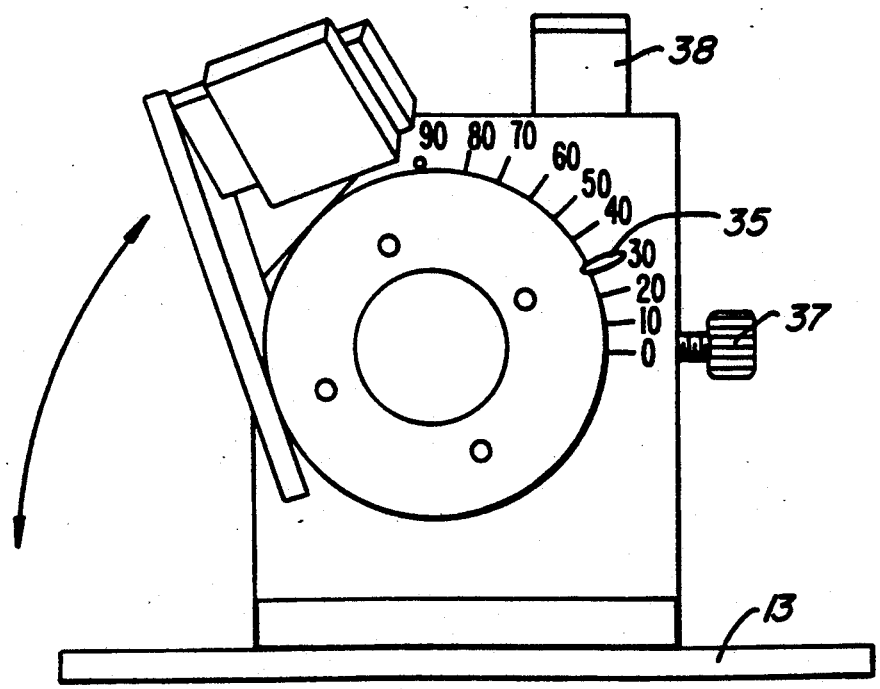

FIGS. 2A and 2B show one of the present invention's rotatable platforms, viewed from approximately the mounting area for the sample holders and looking at the platform. Each platform pivots about its respective beam aperture. By using their respective handles 38, angle selection levers 35, and thumbscrews, the platforms can be rotated to their desired angles and locked into position. Changing their position is a simple matter of releasing the appropriate thumbscrew, readjusting the platform using the appropriate handle, and retightening the thumbscrew.

Figure 3:
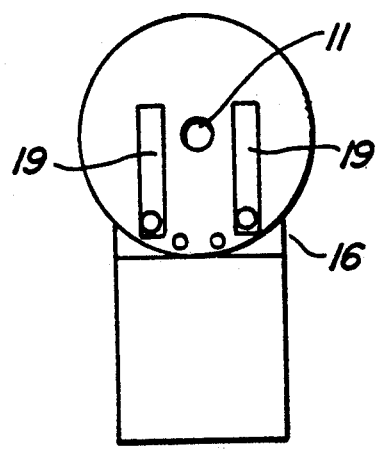
FIG. 3 shows a sample holder for use with the present invention for obtaining a transmission spectrum.
Figure 4:
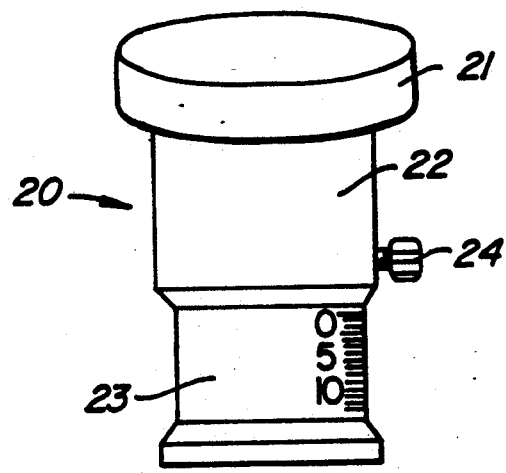
FIG. 4 shows a sample holder for use with the present invention for obtaining a reflectance spectrum.
Figure 5:
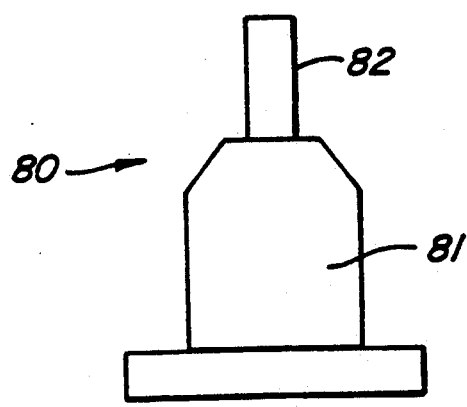
FIG. 5 shows a sample holder for obtaining a reflectance spectrum from a powdered material.

FIGS. 3, 4 and 5 show three types of sample holders. A sample holder 16 for obtaining transmission spectra is shown in FIG. 3. It mounts on pins 15 and has two spring clips 19 for holding the sample and an aperture 11 so that the incoming spectrometer beam can pass through the sample into the output optical train mounted on platform 60. FIG. 4 shows a sample holder 20 for obtaining a reflectance spectrum. It comprises a small platform 21 for holding the sample and telescoping tubes 22 and 23. Adjustment of thumbscrew 24 adjusts the height of sample platform 21 in a known manner. Holder 20 mounts on pins 15. FIG. 5 shows a sample holder 80 for obtaining a reflectance spectrum from a powdered material. Holder 80 comprises base piece 81 which mounts on pins 15 and metal sample holding tube 82 which has a small cup at its tip for holding powdered materials. By reflecting the spectrometer beam from the input optical train off the powdered sample into the output optical train, a reflectance spectrum from the powdered material is obtained.

In operation, the present invention serves as a beam condenser for both transmission and reflection spectrum analysis. The angle of incidence of the incoming spectrometer beam can be varied from about 5° (near normal) to 85° (grazing angle) for reflectance spectra, which also allows for the collection of diffuse reflectance spectrum data at the 45° setting. The use of polarizer 39 enables orientation effects in samples to be analyzed. Furthermore, the use of the polarizer and the positioning of the input and output trains at near-grazing angles (approximately 85°) allows the recording of the reflectance spectra of very thin films on metal substrates. The beam condenser optics (approximately 2½ times) are near optimum for transmittance of spectrum measurements of small samples, such as fibers or micro contaminants. Conversion from transmission to reflection spectrum testing can be done in a matter of minutes by replacing the sample holder and realigning the one adjustable mirror. The entire unit employs kinematic mounting pins for stability, ease of alignment, and rapid accessory interchange. In one embodiment, the present invention is used with an FTS 7/40/60 spectrometer manufactured by the Digilab Division of Bio-Rad Laboratories, Inc.

The two different operating modes require separate alignment procedures. When transmission spectra are to be obtained, the empty transmission holder is placed onto the holder mounting pins. Both angle selection levers are set at 90° (platforms are parallel to baseplate) by loosening the respective thumbscrews, rotating the lever to the 90° setting and retightening the thumb screw. An independent setup program is then run, using the preferred spectrometer. By adjusting adjustable mirror 61, the proper alignment can be achieved.

In reflection spectrum alignment, reflection holder 20 or 80 is mounted on holder mounting pins. A flat shiny gold or silver mirror is then placed on top of the holder and both angle selection levers are set to the desired angle of incidence, in the previously described manner. Once again, a known setup program is run and both mirror 61 and the height of holder 20 or 80 are adjusted until the desired alignment is achieved. Every new sample requires a separate alignment due to differences in the sample thickness. It should be noted that the present invention can also obtain a diffuse reflectance spectrum if the 45° angle of incidence setting is used.

After alignment is completed, spectrum analysis can be performed in a known manner. As either alignment process is relatively simple, obtaining spectra using both transmittance and reflective testing modes can be done in a relatively small amount of time, with little inconvenience.

The present invention has now been described in a preferred embodiment. As many modifications to the present invention can be envisioned without departing from the essential nature of the invention the appended claims, which define the invention, should be read in a broad, inclusive, sense.

What is claimed is:

1. A sample holding apparatus for directing an incoming spectrometer beam, the apparatus comprising:
   base means defining a first plane parallel to the incoming spectrometer beam;
   a first platform pivotally mounted to the base means;
   a beam input optical train mounted to the first platform for directing an input beam onto a sample;
   sample holder means mounted on the base means for holding the sample in the path of the beam from the beam input means; and
   a second platform pivotally mounted to the base means;
   a beam output optical train mounted to the second platform for receiving the beam after it strikes the sample and for transmitting the resultant beam away from the sample for analysis;
   wherein the beam input optical train directs the spectrometer beam directly at the beam output optical train when the first and second platforms are parallel to one another, and wherein the beam input means directs the spectrometer beam toward the base means such that the beam reflects off the sample and at the beam output optical train when the first and second platforms are not parallel to one another.

2. The apparatus of claim 1 wherein the sample holder means comprises a first cylinder mounted on the base means, a second cylinder inserting into the first cylinder, the holder means having means for adjusting the height of the second cylinder relative to the base means, and a sample holder mounted on the second cylinder for holding a sample, the beam going through the sample and sample holder and producing a reflection spectrum.

3. The apparatus of claim 1 wherein the input optical train comprises an input beam aperture, first and second flat mirrors, and a toroidal mirror.

4. The apparatus of claim 1 wherein the output optical train comprises an adjustable flat mirror, a flat mirror, and a toroidal mirror.

* * * * *